United States Patent [19]
Weston

[11] Patent Number: 5,480,381
[45] Date of Patent: Jan. 2, 1996

[54] NEEDLE-LESS INJECTOR

[75] Inventor: Terence E. Weston, Eye, United Kingdom

[73] Assignee: Weston Medical Limited, Suffolk, United Kingdom

[21] Appl. No.: 199,198

[22] PCT Filed: Aug. 21, 1992

[86] PCT No.: PCT/GB92/01539

§ 371 Date: Aug. 4, 1994

§ 102(e) Date: Aug. 4, 1994

[87] PCT Pub. No.: WO93/03779

PCT Pub. Date: Mar. 4, 1993

[30] Foreign Application Priority Data

Aug. 23, 1991 [GB] United Kingdom .................... 9118204

[51] Int. Cl.⁶ .................................................. A61M 5/30
[52] U.S. Cl. .................................................. 604/68
[58] Field of Search ........................................ 604/68–71

[56] References Cited

U.S. PATENT DOCUMENTS

| | | |
|---|---|---|
| 2,762,369 | 9/1956 | Venditty . |
| 2,928,390 | 3/1960 | Venditty et al. ........................ 604/71 |
| 3,330,276 | 7/1967 | Gordon et al. ........................ 128/173 |
| 3,526,225 | 9/1970 | Isobe ........................................ 604/71 |
| 3,802,430 | 4/1974 | Schwebel et al. . |
| 3,859,996 | 1/1975 | Mizzy et al. ............................ 604/71 |
| 4,059,107 | 11/1977 | Iriguchi et al. ................ 128/173 H |
| 4,089,334 | 5/1978 | Schwebel et al. ................... 128/173 |
| 4,592,742 | 6/1986 | Landau . |
| 4,596,556 | 6/1986 | Morrow et al. . |
| 4,642,095 | 2/1987 | Dettbarn et al. ....................... 604/68 |
| 4,722,728 | 2/1988 | Dixon ..................................... 604/68 |
| 4,874,367 | 10/1989 | Edwards . |
| 4,966,581 | 10/1990 | Landau . |

FOREIGN PATENT DOCUMENTS

| | | |
|---|---|---|
| 0034231 | 8/1981 | European Pat. Off. . |
| 0055039 | 6/1982 | European Pat. Off. . |
| 0072057 | 2/1983 | European Pat. Off. . |
| 0107874 | 5/1984 | European Pat. Off. . |
| 0144625 | 6/1985 | European Pat. Off. . |
| 0186916 | 7/1986 | European Pat. Off. . |
| 0219899 | 4/1987 | European Pat. Off. . |
| 0245895 | 11/1987 | European Pat. Off. . |
| 0276158 | 7/1988 | European Pat. Off. . |
| 0307367 | 3/1989 | European Pat. Off. . |
| 0317298 | 5/1989 | European Pat. Off. . |
| 0347190A1 | 12/1989 | European Pat. Off. . |
| 0361668 | 4/1990 | European Pat. Off. . |
| 0368191 | 5/1990 | European Pat. Off. . |
| 0405320A2 | 1/1991 | European Pat. Off. . |
| 0409365A1 | 1/1991 | European Pat. Off. . |
| 0427457A2 | 5/1991 | European Pat. Off. . |
| 0457135A2 | 11/1991 | European Pat. Off. . |
| 0516473A1 | 12/1992 | European Pat. Off. . |
| 0518416A1 | 12/1992 | European Pat. Off. . |
| 0525525A1 | 2/1993 | European Pat. Off. . |
| 0562671A1 | 9/1993 | European Pat. Off. . |
| 0595508A1 | 5/1994 | European Pat. Off. . |
| 1049564 | 12/1930 | France . |
| 0114145A2 | 7/1984 | France . |
| 0258073A1 | 3/1988 | France . |
| 0416975A1 | 3/1991 | France . |
| 8813938 U | 1/1990 | Germany . |

(List continued on next page.)

Primary Examiner—C. Fred Rosenbaum
Assistant Examiner—Frank Wilkens, III
Attorney, Agent, or Firm—Darby & Darby

[57] ABSTRACT

A needless injector having a liquid metering chamber with an outlet orifice, a piston slidable within the metering chamber, and a rod arranged to strike one end of the piston to force liquid through the outlet orifice. A cam follower is mounted at one end of the rod to ride on a cam that retracts the rod away from the piston. The injector is in two parts which are biassed away from each other. The front part of the injector carries the outlet orifice and the rear part carries the cam. Actuation occurs when the two parts of the injector are sufficiently urged towards each other by the user to actuate the cam to release the rod and thereby strike the piston and force liquid through the outlet orifice.

12 Claims, 6 Drawing Sheets

FOREIGN PATENT DOCUMENTS

| | | | |
|---|---|---|---|
| 0718111 | 2/1980 | U.S.S.R. | 604/68 |
| 789029 | 1/1958 | United Kingdom . | |
| 805184 | 12/1958 | United Kingdom . | |
| 915262 | 1/1963 | United Kingdom . | |
| 971162 | 9/1964 | United Kingdom . | |
| 979124 | 1/1965 | United Kingdom . | |
| 993309 | 5/1965 | United Kingdom . | |
| 1052043 | 12/1966 | United Kingdom . | |
| 1327212 | 8/1973 | United Kingdom . | |
| 1382941 | 2/1975 | United Kingdom . | |
| 1449986 | 9/1976 | United Kingdom . | |
| 1528735 | 10/1978 | United Kingdom . | |
| WO82/02835 | 9/1982 | WIPO . | |
| WO85/02775 | 7/1985 | WIPO . | |
| WO85/02776 | 7/1985 | WIPO . | |
| WO86/00815 | 2/1986 | WIPO . | |
| WO89/08469 | 9/1989 | WIPO . | |
| WO89/12473 | 12/1989 | WIPO . | |
| WO91/01153 | 2/1991 | WIPO . | |
| WO91/02557 | 3/1991 | WIPO . | |
| WO91/13689 | 9/1991 | WIPO . | |
| WO91/12839 | 9/1991 | WIPO . | |
| WO91/16094 | 10/1991 | WIPO . | |
| WO92/08508 | 5/1992 | WIPO . | |
| WO92/12747 | 8/1992 | WIPO . | |
| WO92/12745 | 8/1992 | WIPO . | |
| WO92/20388 | 11/1992 | WIPO . | |
| WO92/19296 | 11/1992 | WIPO . | |
| WO92/22338 | 12/1992 | WIPO . | |
| WO93/13819 | 7/1993 | WIPO . | |
| WO93/23098 | 11/1993 | WIPO . | |

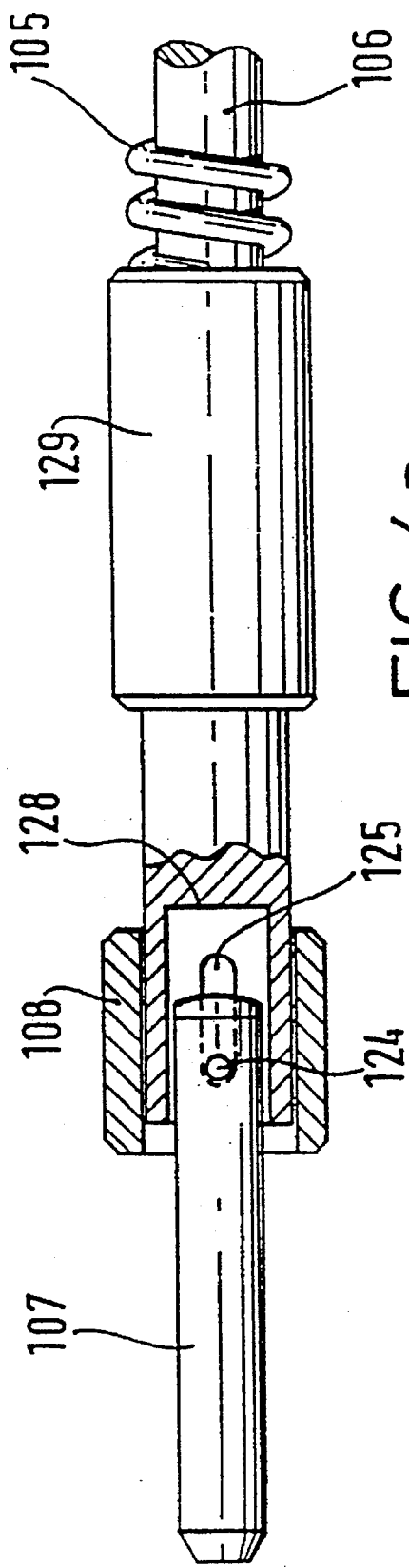
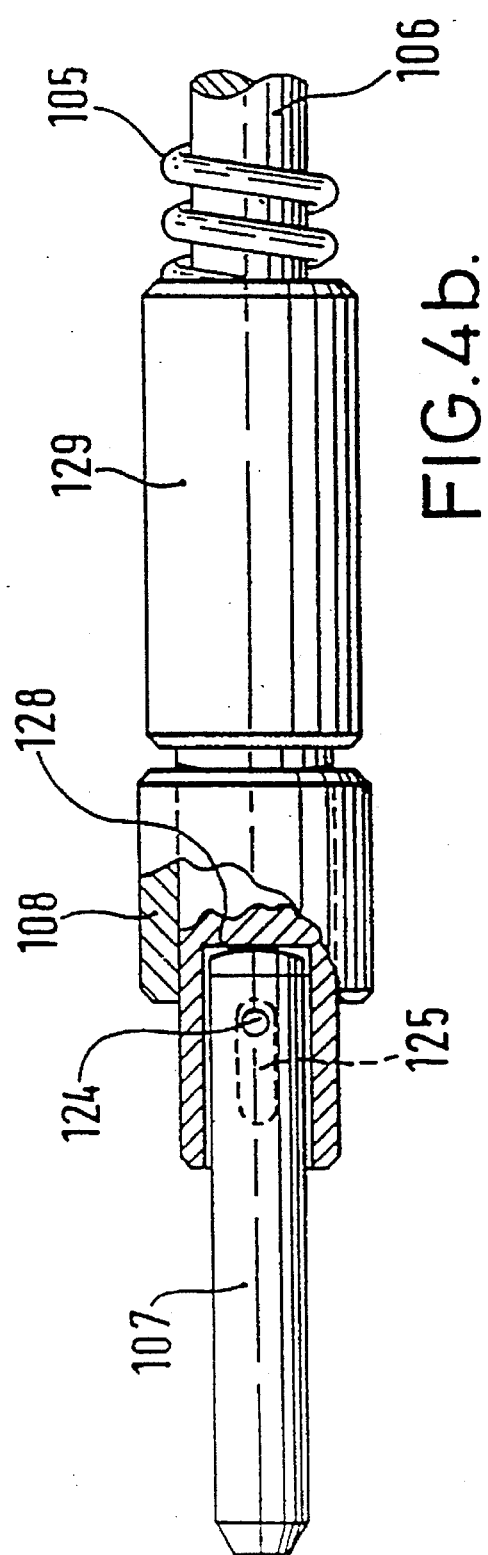
FIG. 4a.
FIG. 4b.

NEEDLE-LESS INJECTOR

BACKGROUND OF THE INVENTION

The present invention relates to a needle-less injector, preferably a multi-dose injector, wherein a dose of liquid medicament is discharged in a thin jet at sufficient velocity to penetrate the epidermis of the human, animal or plant to be treated, thus to introduce the medicament into the tissues of the subject.

Needle-less injectors are used as an alternative to hypodermic needle type injectors for delivering drugs, vaccines, local anaesthetics and other fluids into the tissues. The medicament is discharged in a jet at high velocity to first puncture the epidermis and thereafter be deposited in the tissues of the subject. A variation is to press the discharge nozzle onto the epidermis and force the liquid at very high pressure through the epidermis.

Prior art devices typically employ a spring-loaded piston pump to generate the injection pressure, in which the piston is retracted against a spring to withdraw fluid from a reservoir. At the end of the piston stroke (which may be adjustable) the piston is disengaged from the retracting mechanism and is urged suddenly by the spring to pressurise and discharge the fluid from the delivery nozzle. The retracting or loading operation may be manual or motorised. In other devices, the piston is driven on the discharge stroke by gas or electric motor instead of a spring.

Manually operated injectors generate a pressure in the medicament of about 100 bars. In operation, the discharge orifice is placed a small distance (about 1 cm) from the epidermis, and the high velocity jet strikes and then penetrates the epidermis (the free jet mode). The principle appears to be that the jet sacrifices some of its kinetic energy to puncture the epidermis, because if the discharge orifice is placed firmly on the skin, and the injector is operated, the liquid is pressurised but has no kinetic energy, ant is unable to pierce the skin. In the free jet mode, medicament is wasted, since some of the liquid is deflected sideways before the puncture is completed, whilst in the contact mode, the epidermis deforms under the pressure of the liquid, which allows all of the liquid to escape without achieving penetration.

Powered injectors generate higher pressures— typically 400 bars or more, which is sufficient to penetrate the epidermis even when the discharge orifice is placed firmly on the skin (the contact mode). However, even in the contact mode a variable quantity of liquid is lost on each injection because the epidermis initially deforms before puncturing, and allows some liquid to escape.

Laboratory tests on both manual and powered injectors often give encouraging results, but in practical situations, such as the vaccination of animals, very variable amounts are injected—frequently over 50% of the vaccine may be wasted—because of hairs and dirt on the injection site, and movement of the animal. The difficulty in achieving successful injections is exacerbated if the subject does not co-operate, as in the case of animals. Premature operation of the injector is common, as is relative movement between the epidermis and orifice which can cause tearing of the epidermis during injection.

Various methods have been proposed to overcome these problems, although in the case of the free jet types, little can be achieved. Powered injectors often employ a vacuum device to suck the epidermis firmly onto the discharge orifice (see WO 82/02835—Cohen, and EP-A-347190 —Finger) and thereby improve the seal between the orifice and skin, and prevent relative movement. Alternatively, a pressure sensitive sleeve on the injector (see U.S. Pat. No. 3,859,996 —Mizzy) is placed on the subject, whereby operation of the injector is prevented until the correct contact pressure between the orifice and skin is achieved. The basic aim of such devices is to stretch the epidermis over the discharge orifice, and apply the pressurised medicament at a rate which is higher than the epidermis will deform away from the orifice—i.e. the rate of application of the liquid must be higher than the resonant frequency of the epidermal layer. This condition is not often achieved, and some leakage still occurs.

Powered injectors naturally have available a variety of sensing and control devices to enhance their performance, which are denied to manually operated injectors. However, they are invariably more complex and not easily adapted for portable use. The fact that they generate higher pressures than the manual devices means that their power consumption is high; gas powered injectors require a heavy cylinder of compressed gas, and electrical injectors are often mains powered. Furthermore, the sensing methods used to enable optimum operation are invariably indirect or secondary. For example, U.S. Pat. No. 3,859,996 —(Mizzy) discloses a controlled leak method to ensure that the injector orifice is correctly placed at the required pressure on the subject's skin. When the placement conditions are met, the controlled leak is sealed off by contact with the subject's skin, and the pressure within the injector control circuitry rises until a pressure sensitive pilot valve opens to admit high pressure gas to the drive piston. However, the actual pressure of the discharge orifice on the skin is not being measured; a hair or dirt on the sealing face of the controlled leak orifice will prevent or retard the pressure rise in the control circuit, and the operator will unconsciously press the injector harder onto the skin. Also, the timing characteristics may vary because of ineffective sealing, hysteresis of the pressure switch and variations in the gas supply pressure. In other words, the parameters being measured are the effectiveness of the seal of the controlled leak sensor on the skin and the pilot valve response, not the actual pressure of the orifice on the epidermis. Still other devices use a sliding sleeve in contact with the subject, whereby the displacement of the sleeve is used to initiate the injection, but this method measures the load on the sleeve, not on the orifice as required. Again, there can be considerable difficulty when using such injectors on livestock.

It may be seen therefore that whilst needle-less injection potentially is more efficient than hypodermic needle injectors for certain applications, the technique is very dependent on the ability of the operator and the compliance of the subject to be injected. Those injectors that have features designed to reduce the problems tend to be more complex and costly, and less portable.

SUMMARY OF THE INVENTION

It is an object of a first aspect of the invention to provide a means of pressurising the medicament at a sufficiently high rate to pierce the epidermis before it has time to deform away from the orifice. It is an object of a second aspect of the present invention to overcome the problems of repeatability and inconvenience of prior art devices by directly sensing that the pressure of the discharge orifice on the subject's epidermis is at a predetermined value so as to permit operation of the injector.

According to the first aspect of the invention there is provided a needle-less injector which comprises a chamber for containing liquid to be injected, the chamber being provided with a liquid outlet; a dispensing member movable in a first direction to reduce the volume of the chamber to cause liquid contained therein to be expelled through the said liquid outlet; and an impacting member arranged to strike the said dispensing member to cause movement thereof in the said first direction.

Preferably the dispensing member is a piston, and the impacting member comprises a mass which is biassed in a direction to strike the piston, but is prevented from doing so, prior to operation, by a latch, for example a cam and cam follower mechanism. There is a gap between the piston and the mass, so that when the spring is released for the injection, the mass strikes the piston. The impact force thus produced is rapidly transmitted through the liquid medicament (which is nearly incompressible) and appears at the discharge orifice. The extremely high rate of pressure increase is sufficient for the liquid medicament to easily puncture the epidermis, whilst the remainder of the piston stroke propels the liquid through the punctured epidermis, to a depth controlled by the pressure produced in the remainder of the piston stroke. An analogy may be drawn by considering a nail: considerable force is necessary to merely push a nail into a piece of wood, whereas a relatively light impact caused by a hammer will cause the nail to penetrate the wood. The present invention provides, in effect, "liquid nail" the point of which is defined by the geometry of the discharge orifice.

According to the second aspect of the invention there is provided a needle-less injector which comprises a chamber for containing liquid to be injected, the chamber being provided with a liquid outlet; means for expelling liquid through the said outlet; a front portion which carries means defining said liquid outlet, a rear portion having means defining a handle for the injector, means for urging the rear portion away from the front portion, and means for actuating the injector, or permitting actuation thereof, in response to movement of the rear portion towards the front portion against the force of the means urging them away from one another.

The discharge orifice is placed onto the epidermis, and hand pressure is applied via the urging means, preferably a substantially co-axial compression spring. Predetermined displacement of the spring mounting relative to the orifice (and therefore the pressure applied) actuates a device to release the latch, thereby causing the spring to suddenly force the piston onto the medicament to create a rapid pressure rise. Hence the actual pressure applied on the epidermis directly operates the release mechanism.

Thus it may be seen that the present invention, if the two aspects described above are combined, employs direct sensing to ensure the optimum pressure of the injector onto the subject's skin, and the injection cycle is comprised of an initial impact to pierce the epidermis, followed by a lower pressure delivery of the medicament into the tissues.

According to one embodiment of the invention there is provided a piston sealingly and slidingly located in a cylinder having inlet and outlet ports connected via non-return valves to a reservoir of liquid and a discharge orifice respectively. The piston is connected by a sliding, lost motion, link to a mass which it itself abuts and which is urged by a spring. When the mass is retracted against the spring, a gap is formed between the mass and the piston, which dimension is determined by the sliding link.

Further retraction of the mass drags the piston out of the cylinder to create a depression, causing liquid to flow from the reservoir into the cylinder. The mass is latched into the loaded position until released by the trigger means. On release, the mass is rapidly accelerated by the spring and strikes the piston to create a near instantaneous pressure rise in the liquid, as previously described. Preferably the retracting and release means comprises a cylindrical cam driven by an electric motor-gearbox, the operation being controlled by tripping a microswitch by relative movement of the orifice contacting pressurising means, which pressure is adjustable.

Instead of an electric motor for retracting the mass against the spring, other means may be used, for example manual means or a gas powered motor.

In a preferred embodiment of the invention there is provided a manually operated trigger acting in series with the pressure sensing trigger, so as to minimise the possibility of accidental operation of the injector.

Where the injector is powered, a replaceable power source may be provided within the injector, or the injector may be connected to an external power source.

The injector may be provided with a detachable reservoir for the liquid.

BRIEF DESCRIPTION OF THE DRAWINGS

In the accompanying drawings:

FIGS. 4a and 4b show part of the embodiment of FIG. 3 on an enlarged scale, showing the two extreme positions of a piston and a connecting rod;

DETAILED DESCRIPTION OF THE PREFERRED EMBODIMENT

Figure 1:
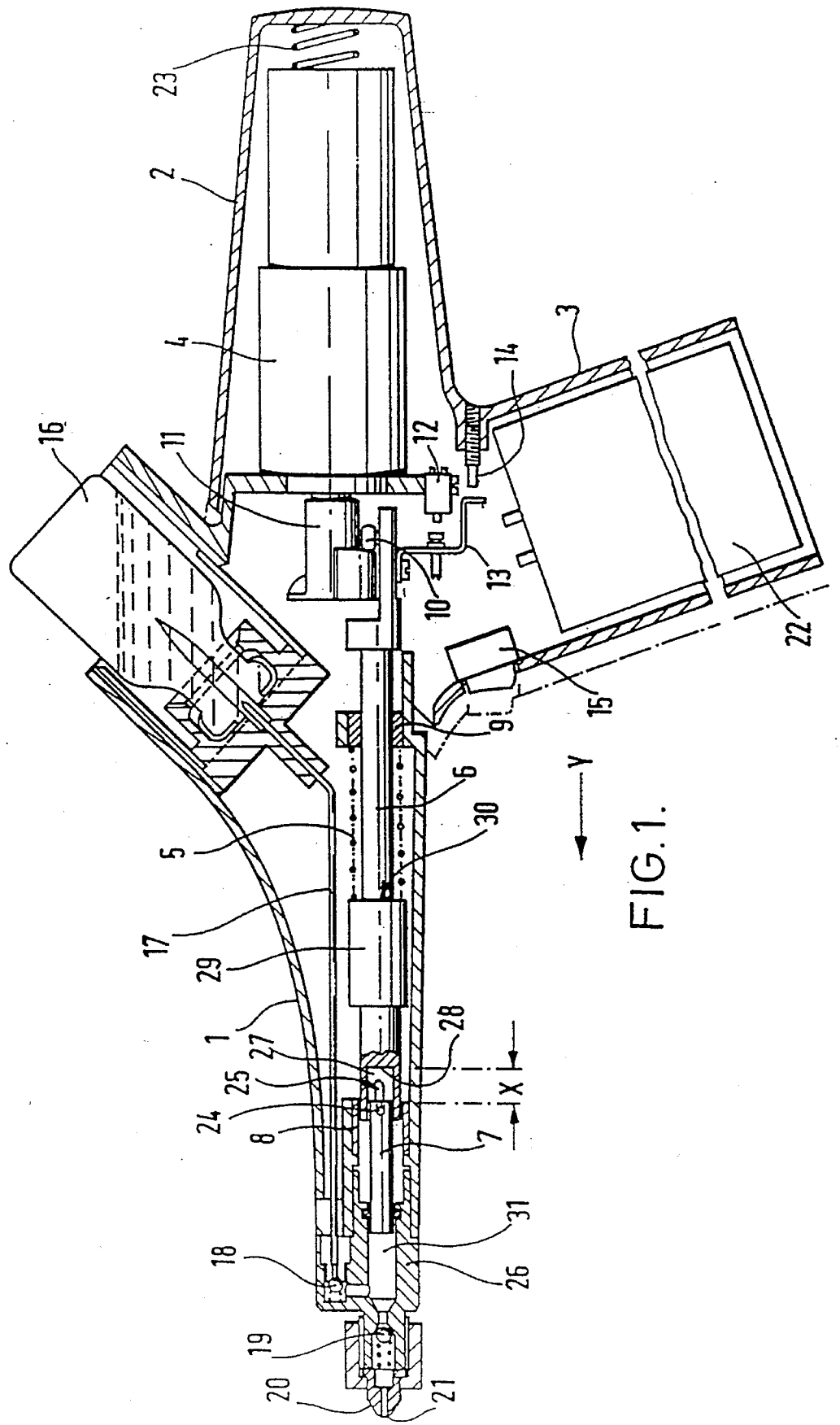
FIG. 1 shows a first embodiment of an injector according to the invention, partly in longitudinal section and partly cut away, with the components positioned just before injection.

The injector shown in FIG. 1, comprises an outer casing having a front section 1 and a rear section 2. Section 2 may be displaced along the longitudinal axis of the injector relative to section 1, from which it is urged apart by a spring 23. The sections are held together against the force of the spring by a restraining block which is not shown in FIG. 1 but which is of similar form to the block shown in FIG. 3 in relation to a second embodiment. The front end of section 1 supports a cylinder 26 in which a piston 7 is sealingly located. The piston 7 is preferably hollow, but closed at both ends, in the case of the righthand end by a hard cap. The cylinder 26 is connected via a non-return valve 18, biassed to its closed position by a compression spring, and a tube 17 to a reservoir 16 containing a liquid to be injected. The reservoir has an air inlet (not shown) to permit air to enter the bottle as the liquid is dispensed therefrom. A discharge nozzle 20 is sealingly connected to the cylinder 26, and a non-return valve 19, biassed to its closed position by a compression spring, prevents air being drawn into the cylinder during the induction stroke.

The piston 7 is loosely located within a hole 27 in the end of a connecting rod 6, so that it may move freely in a longitudinal direction. A pair of pins 24 is fixed to the piston 7, the pins extending radially therefrom on opposite sides thereof. Each pin slides in a slot 25 in the connecting rod 6. In the extreme leftward position of the piston 7, the pins 24 are at the lefthand ends of their respective slots. However, in the extreme righthand position of the piston 7 the pins do not reach the righthand ends of their respective slots. That position is defined by a face 28 at the end of hole 27, the righthand end of the piston 7 meeting that face before the pins can reach the righthand end of their slots. The connecting rod 6 is slidingly located in bearings 8 and 9, and urged in the forward direction by a compression spring 5 one end of which acts on a face 30 of a mass 29 which is integral with the connecting rod 6. A distinct mass 29 which is identifiable as such is not always necessary for example if the mass of the rod 6 itself is sufficient. The other end of the spring 5 reacts against the end face of the bearing 9.

A motor-gearbox assembly 4 is housed in casing section 2 but attached to front section 1 and the output shaft carries a cylindrical cam 11 to which is engaged a follower 10 attached to the connecting rod 6. The motor is described below as being electric, but could be of some other type, for example gas powered. A resilient microswitch trip 13 is mounted on the connecting rod 6, so that when the connecting rod 6 is retracted against the spring 5 (by rotation of the cam 11), at a predetermined position, the trip 13 operates a normally closed microswitch 12 attached to the front section 1.

The rear section 2 has a handle part 3 which houses an electrical battery 22 and a trigger switch 15. The battery is connected in series with the trigger switch 15, the microswitch 12 and the motor 4.

Figure 2:
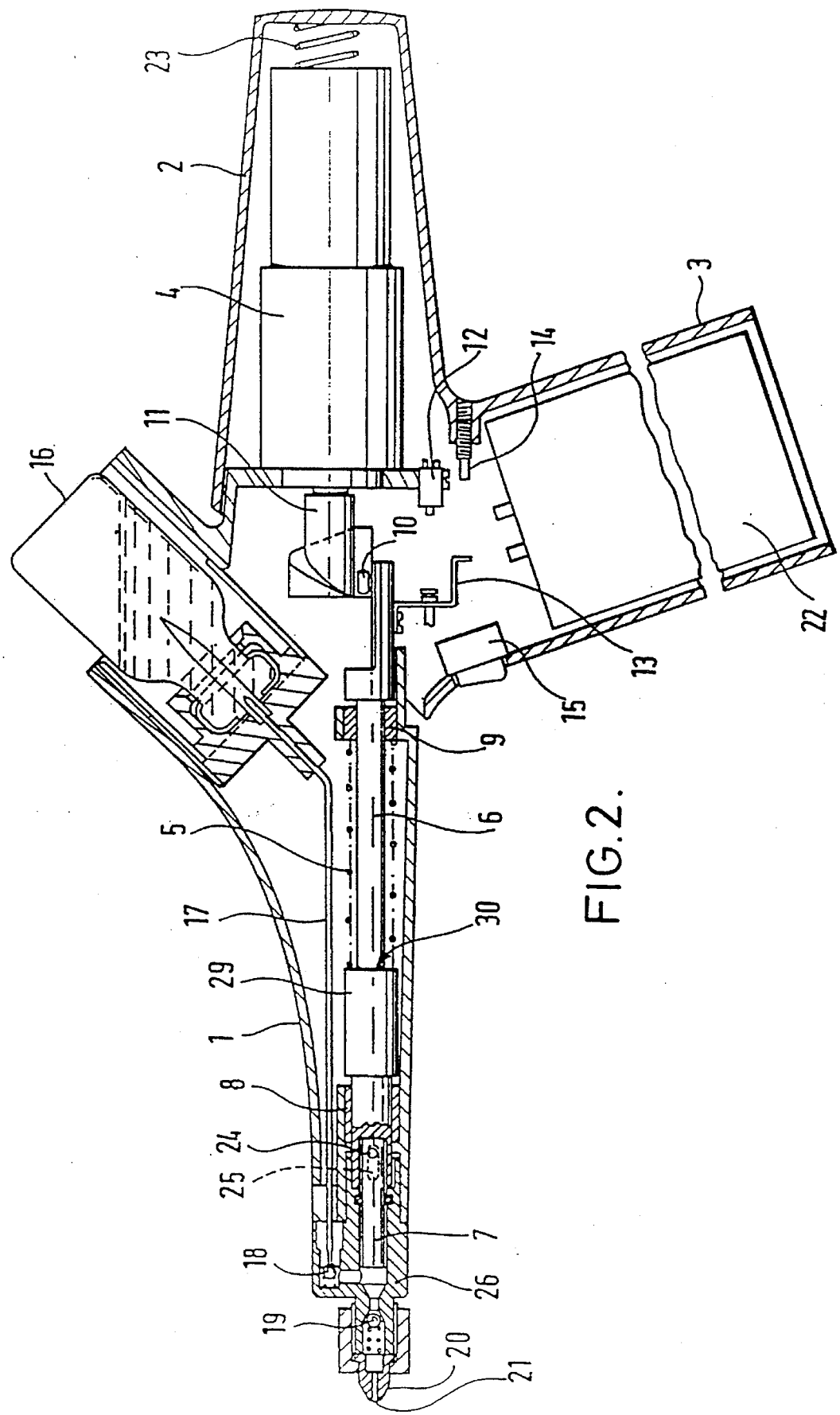
FIG. 2 is a view corresponding to FIG. 1 but showing the components immediately after injection.
Figure 6:
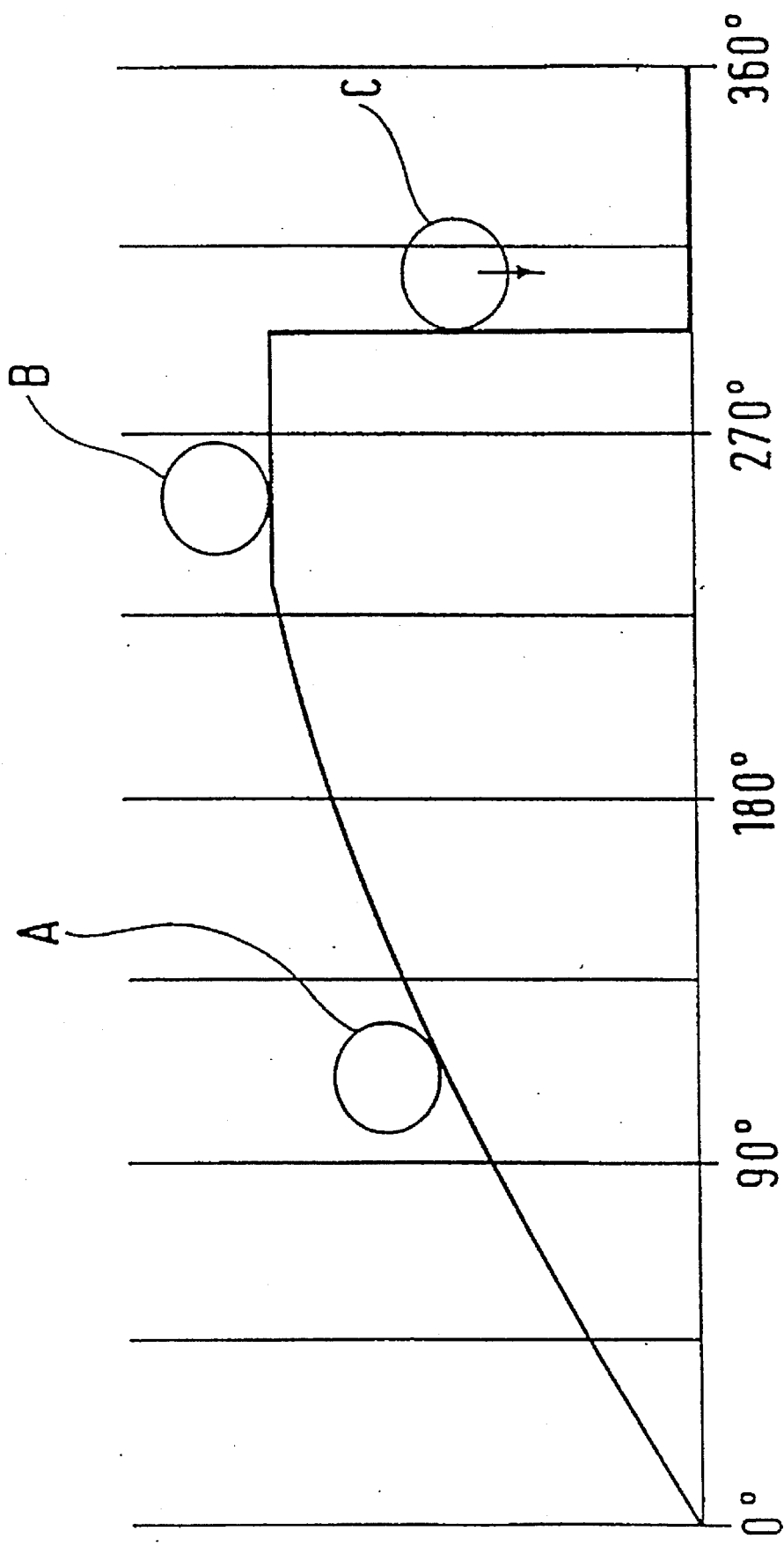
FIG. 6 is a cam timing sequence diagram for the first embodiment, with the abscissa representing cam rotation in degrees.

Referring to FIG. 2 (which shows the injector in the discharged condition) the trigger switch 15 is operated, and the motor 4 is energised and rotates cam 11 which retracts connecting rod 6 against spring 5. During retraction the cam follower travels along the sloping portion of the cam profile shown in FIG. 6. The reference A in FIG. 6 denotes the position of the cam follower part way through this travel. As the connecting rod retracts, the piston 7 initially remains stationary, until the lefthand ends of the slots 25 in connecting rod 6 are contacted by the pins 24 in piston 7. The piston then travels with the connecting rod 6 and draws injection liquid from reservoir 16 into a metering chamber 31 defined in the cylinder 26 between the valve 19 and the lefthand end of the piston 7. As the cam follower reaches the maximum stroke position, trip 13 operates microswitch 12 to switch off the motor 4. The cam follower is now on a substantially zero lift or parallel part of the cam, and is thereby retained in a "latched" position (denoted by B in FIG. 6), and the injector is loaded ready for use.

Referring also to FIG. 1, to cause an injection the trigger switch 15 is depressed, and the nozzle 20 containing orifice 21 is placed on the subject to be injected, and pressure is applied by pushing on handle 3 in the direction of arrow Y. The rear section 2 is thus displaced relative to the front section 1, and the pressure applied to the subject by nozzle 21 is proportional to the compression of spring 23. At a predetermined amount of displacement, a screw 14 secured to the rear section 2 contacts and moves trip 13 away from the microswitch 12. This causes the battery 22 to be connected to the motor 4, which then rotates the cam 11. After a few degrees of rotation, the cam follower 10 is suddenly released by the cam profile (reference C in FIG. 6), and the connecting rod 6, with its mass 29, is rapidly accelerated by the spring 5. After travelling a distance "X" (see FIG. 1), the face 28 on connecting rod 6 hits the end of piston 7 with considerable impact. The force of this impact is almost instantaneously transmitted through the liquid in the metering chamber 31, causing the liquid to travel rapidly past the valve 19 and through the orifice 21, which is in contact with the subject. This initial impact of the liquid easily pierces the epidermis of the subject, and the remainder of the piston travel completes injecting the dose of liquid at relatively low pressure.

During the complete injection stroke of the connecting rod 6, which is accomplished extremely rapidly, the cam 11 continues rotating and picks up the cam follower 10, thereby retracting the connecting rod 6 until the trip 13 contacts microswitch 12 to turn off motor 4. Thus the metering chamber 31 is loaded ready for the next injection.

The screw 14 may be adjusted to alter the amount of displacement of section 2 relative to section 1 (and therefore the compression of spring 23) before the microswitch 12 is operated. Thus a very simple adjustment directly controls the pressure of the discharge orifice 21 on the subject. It is necessary for the rear section 2 to be freely movable with respect to section 1, so that the pressure on the subject is not altered by the effects of friction.

One rotation of the cam retracts, latches and releases the spring loaded piston, and the use of the cam permits very simple, accurate and reliable operating characteristics, and a high rate of injections may be achieved with no fatigue of the operator. Furthermore, the injector operation is easy to understand and maintain by unskilled persons.

The following dimensions and specifications have been used for an injector that gave excellent results when used for intradermal injections in pigs.

| | |
|---|---|
| Diameter of piston 7 | 5 mm |
| Stroke of piston 7 after impact by rod 6 | 9 mm |
| Stroke of rod 6 before impact with piston 7 (Total stroke 15 mm) | 6 mm |
| Injection orifice 21 | 0.25 mm × diameter × 0.5 mm long |
| Injection volume | 0.17 ml |
| Injection spring rate of spring 5 | 7N/mm |
| Preload of spring 5 | 105N |
| Final load of spring 5 | 210N |
| Accelerated weight of rod 6/mass 29 | 64 g |
| Impact momentum approx. | 93 g · m/s |
| Injection fluid | oil emulsion vaccine |
| Battery 22 | Ni—Cad 12 v × 260 mAh |
| Number of injections per charge | 1500 at 1200 injections/hour |
| Maximum injection rate | 100/minute |
| Nozzle contact force | 3N |

With good practice, a compliant pig, and choosing an optimum injection site on the animal such as the back of the neck, wastage is negligible. However, in an ordinary situation, typically between one and two per cent of the vaccine is wasted in each injection, compared with at least 50% wasted with conventional manually operated injectors.

Figure 3:
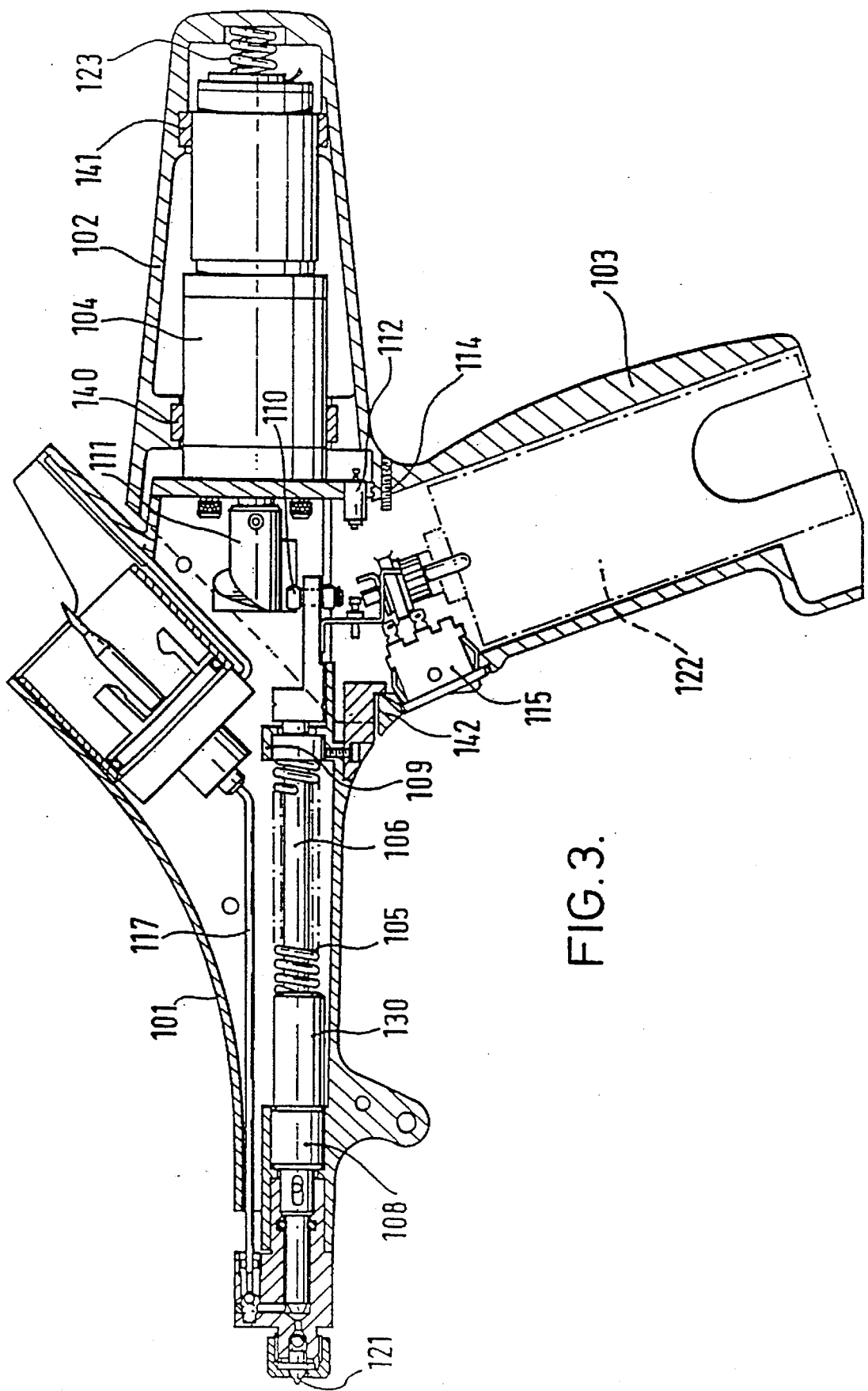
FIG. 3 shows a second embodiment in a position intermediate that of FIGS. 1 and 2 in the case of the first embodiment.
Figure 5:
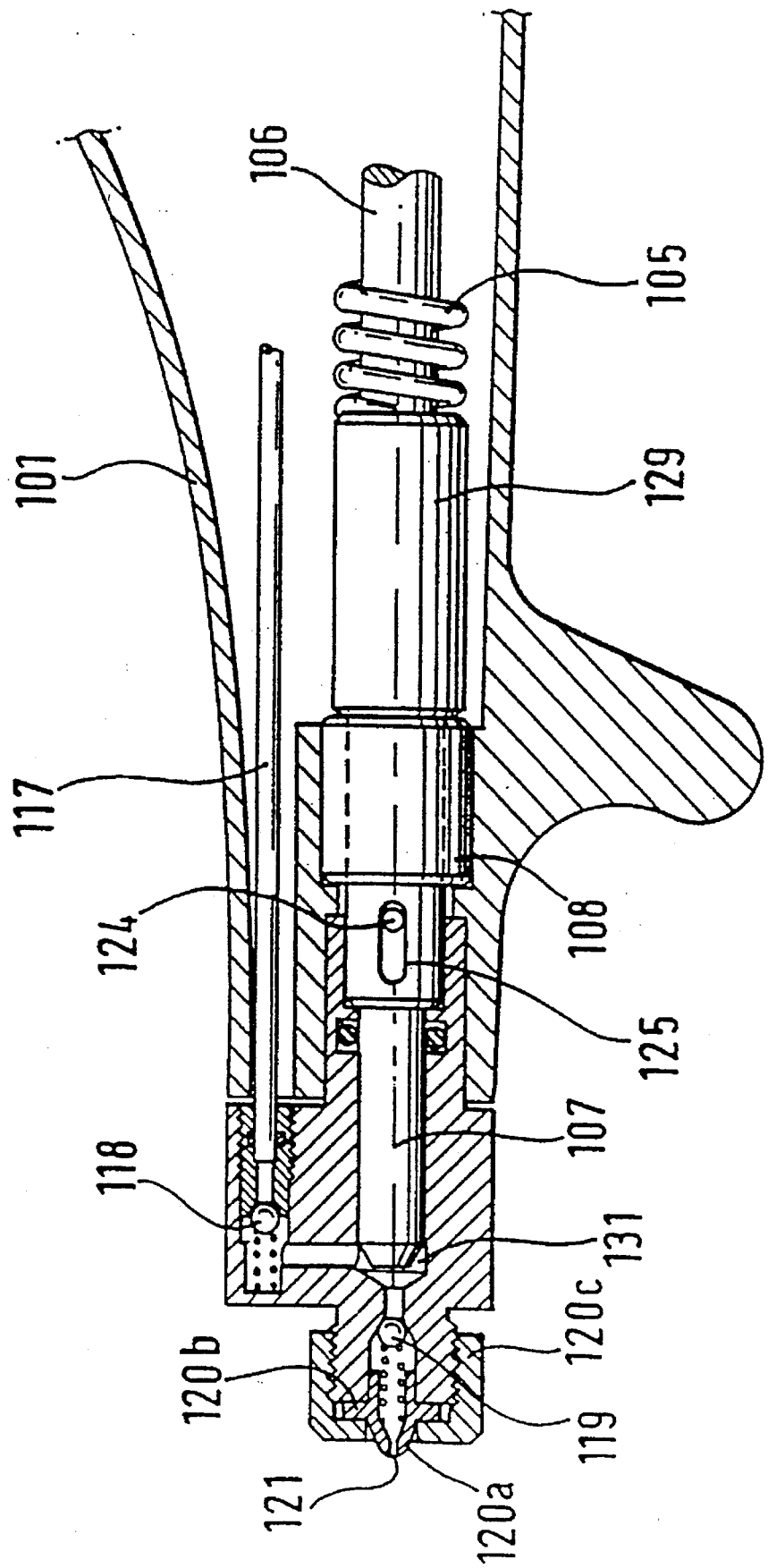
FIG. 5 shows the front end of the embodiment of FIG. 3, on a larger scale.

The second embodiment shown in FIGS. 3 to 5 is very similar to that shown in FIGS. 1 and 2, and corresponding elements are denoted by the same reference numerals but with the addition of 100.

The embodiment of FIGS. 3 to 5 is shown without a container corresponding to container 16 in the first embodiment, but it is understood that such a container would be present. Some other aspects of the second embodiment, however, are shown in more detail that is the case for the first embodiment. Thus, the external form of the casing sections 101 and 102 are shown in a more practical and less diagrammatic form than the casing sections 1 and 2. Also, the interior of the casing section 102 is shown as having support bearings 140 and 141 in which the motor 104 is slidable, and the casing section 102 is shown as being provided with a restraining block 142 to prevent the sections 101 and 102 separating under the force of the spring 123. In practice the first embodiment would be provided with bearings corresponding to the bearings 140 and 141, and (as already mentioned) with a restraining block corresponding to block 142.

The second embodiment has an outlet nozzle somewhat different to that of the first embodiment. Thus, the outlet nozzle 120 comprises a frustoconical tip portion 120a with an orifice 121 therein, and a flange portion 120b by means of which the nozzle 120 is held in place using an internally threaded retaining cap 120c.

The embodiment just described is just one of several methods that may be employed to cause an impact on the liquid in order to facilitate the initial puncturing of the epidermis, and those skilled in the art will readily be able to adapt both manual injector designs, and other powered injector designs to achieve the object of the invention. Equally, the principle of the direct orifice contact loading may easily be adapted to manual injectors, for instance by moving a sear to release the spring loaded mass, and to gas-powered injectors, for example by employing a fluid power microswitch in a similar manner to the embodiment herein.

The present invention may be used with any suitable form of liquid reservoir mounted on the injector, including, but not limited to, rigid bottles, syringes, collapsible tubes and sachets, or the injector may be connected to an external supply of liquid. Whilst portable, multi-dose injectors are described in detail above, the present invention may be effectively applied to fixed installations, such as used for the multiple vaccination of poultry, and single dose injectors that use a pre-packed capsule of liquid that is discarded after injection (see U.S. Pat. No. 4,966,581—Landau).

During tests carried out on the second embodiment described above, it was noticed that even if the orifice was held some 2-3 mm away form the subject's skin, the wastage was considerably less than that when using manually powered free jet injectors. Thus, for some applications where it is desirable that the orifice does not contact the skin of the subject, the impact technique improves the performance of free jet injectors.

I claim:

1. A needle-less injector comprising:

a chamber defined within said injector for containing liquid to be injected;

a front portion having means defining a liquid outlet for said chamber;

a rear portion having means defining a handle for said injector;

a dispensing member in contact with the liquid in said chamber and movable in a first direction to reduce the volume of said chamber to cause the liquid contained therein to be expelled through said liquid outlet;

an impacting member arranged to strike said dispensing member to cause movement thereof in said first direction;

means for resiliently urging said rear portion away from said front portion; and means for actuating said injector, or permitting actuation thereof, in response to the application of a selected amount of axial pressure to said front portion to cause said front portion to move towards said rear portion against the force of said means for resiliently urging.

2. An injector according to claim 1, comprising means for holding the said impacting member away from the said dispensing member, against a biasing force, and for releasing the said impacting member to permit it to travel towards, and impact against, the said dispensing member.

3. An injector according to claim 2, wherein the biassing force is provided by a spring.

4. An injector according to claim 2, wherein the means for holding and releasing the said impacting member comprises a latch means.

5. An injector according to claim 4, wherein the latch means comprises a cam and a cam follower.

6. An injector according to claim 5, comprising a motor for driving the said cam.

7. An injector according to claim 1, wherein the said dispensing member is a piston movable within the said chamber.

8. An injector according to claim 1, wherein the dispensing member and the impacting member are interconnected by a lost motion connection.

9. An injector according to claim 8, wherein the lost motion connection comprises at least one slot formed in one of the said members, and at least one cooperating pin provided on the other of the said members and movable lengthwise of the slot with which it cooperates.

10. An injector according to claim 9, wherein each pin engages one end of the slot with which it cooperates to allow the impacting member to move the dispensing member in a second direction opposite to said first direction, but in which, during dispensing, the impacting member strikes the dispensing member before the pin is able to engage the other end of the slot.

11. An injector according to claim 1, adapted to draw the liquid to be injected from a liquid source capable of providing a plurality of doses thereof.

12. An injector according to claim 11, comprising valve means for allowing liquid to be drawn into the said chamber from the liquid source during movement of the dispensing member in said second direction, and for preventing liquid being returned to the liquid source during movement of the dispensing member in said first direction.

* * * * *

UNITED STATES PATENT AND TRADEMARK OFFICE
CERTIFICATE OF CORRECTION

| | | |
|---|---|---|
| PATENT NO. | : 5,480,381 | Page 1 of 1 |
| APPLICATION NO. | : 08/199198 | |
| DATED | : January 2, 1996 | |
| INVENTOR(S) | : Terence E. Weston | |

It is certified that error appears in the above-identified patent and that said Letters Patent is hereby corrected as shown below:

In the Title page item [54], line 1, please correct "needless" to read --needleless--.

Signed and Sealed this

Fifteenth Day of September, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 5,480,381 | Page 1 of 1 |
| APPLICATION NO. | : 08/199198 | |
| DATED | : January 2, 1996 | |
| INVENTOR(S) | : Terence E. Weston | |

It is certified that error appears in the above-identified patent and that said Letters Patent is hereby corrected as shown below:

In the Title page item [57], Abstract, line 1, please correct "needless" to read --needleless--.

This certificate supersedes the Certificate of Correction issued September 15, 2009.

Signed and Sealed this

Thirteenth Day of October, 2009

David J. Kappos
*Director of the United States Patent and Trademark Office*